United States Patent [19]
Padden et al.

[11] Patent Number: 5,319,986
[45] Date of Patent: Jun. 14, 1994

[54] SAMPLER WITH MAGAZINE SYSTEM

[75] Inventors: Harvey F. Padden, Pompton Lakes; Frank C. Rumore, Mahwah, both of N.J.

[73] Assignee: Computer Control Corporation, Pompton Plains, N.J.

[21] Appl. No.: 92,280

[22] Filed: Jul. 15, 1993

Related U.S. Application Data

[63] Continuation of Ser. No. 661,009, Feb. 26, 1991, abandoned.

[51] Int. Cl.$^5$ .......................... G01N 35/02; B01L 3/14
[52] U.S. Cl. ................ 73/863.21; 73/864.91; 422/104
[58] Field of Search ........... 73/863.01, 863.21, 863.23, 73/863.24, 863.25, 863.71, 864.34, 864.35, 864.91; 55/270; 422/63, 64, 65, 104; 436/45, 47, 48, 49

[56] References Cited

U.S. PATENT DOCUMENTS

| | | | |
|---|---|---|---|
| 3,712,144 | 1/1973 | Kuzel et al. | 73/863.71 |
| 3,778,232 | 12/1973 | McMorrow, Jr. | 422/65 |
| 3,823,602 | 7/1974 | Anderson | 55/270 |
| 4,046,011 | 9/1977 | Olsen | 73/864.35 |
| 4,055,396 | 10/1977 | Meyer et al. | 422/104 |
| 4,141,444 | 2/1979 | Kulberg et al. | 198/740 X |
| 4,155,711 | 5/1979 | Zelagin et al. | 422/65 X |
| 4,219,530 | 8/1980 | Kopp et al. | 422/69 |
| 4,478,095 | 10/1984 | Bradley et al. | 73/864.23 |
| 4,481,297 | 11/1984 | Zucal et al. | 73/863.21 |
| 4,759,227 | 7/1988 | Timmons | 73/864.34 |
| 4,799,394 | 1/1989 | Barnett et al. | 73/863.01 |
| 4,944,781 | 7/1990 | Ruggirello et al. | 73/23.41 X |
| 4,974,458 | 12/1990 | Koike | 73/864.25 |
| 5,055,271 | 10/1991 | Golias et al. | 73/863.31 X |
| 5,171,531 | 12/1992 | Christianson et al. | 422/64 |

FOREIGN PATENT DOCUMENTS 244377  10/1987  Japan.

*Primary Examiner*—Thomas P. Noland
*Attorney, Agent, or Firm*—Ostrolenk, Faber, Gerb & Soffen

[57] ABSTRACT

A tube magazine for a sampling system has a plurality of sampler tube receiving spaces for receiving sampler tubes. The sampler tubes can be separated from the system as a unit, and transported to another location for analysis. A first part of the system includes a plurality of introducing devices disposed for introducing gaseous fluid into corresponding ones of the sampler tubes; and a second part which forms with the sampler tubes a replaceable magazine which is readily removable from the first part, whereby the corresponding introducing devices and receiving spaces are simultaneously brought into fluid communication when the first and second parts are connected together. Advantageously, each of the sampler tube receiving spaces has a central, elongated axis, the axes of the sampler tube receiving spaces being parallel to each other; a trap tube receiving space for receiving a trap tube, the trap tube receiving space being surrounded by the sampler tube receiving spaces, the trap tube receiving space having an elongated, central axis which is parallel to the axes of the sampler tube receiving spaces; and a common end space for providing fluid communication between the trap tube receiving space and each of the sampler tube receiving spaces. A selector valve system can be provided for selectively introducing fluid into the sampler tube receiving spaces.

24 Claims, 3 Drawing Sheets

SAMPLER WITH MAGAZINE SYSTEM

This is a continuation of application Ser. No. 07/661,009 filed on Feb. 26, 1991, now abandoned.

BACKGROUND OF THE INVENTION

The present invention relates to a system for taking samples of a fluid, particularly, a system for taking samples of air or another gas at a remote location at specified periods of time. Prior art systems have been developed for this purpose, but these systems have proven to be less than fully satisfactory.

SUMMARY OF THE INVENTION

An object of the present invention is to provide an improved system for taking samples, particularly, a system which is compact, accurate, efficient and convenient.

Thus, the present invention relates to a sampler magazine system which has a plurality of sampler tube receiving spaces for receiving sampler tubes and which is arranged such that the sampler tubes can be separated from the system along with a magazine part and transported to a second location for analysis.

Preferably, the system also has a trap tube receiving space which is surrounded by the sampler tube receiving spaces, and a common end space for providing fluid communication between the trap tubes and the sampler tubes. In operation, the fluid flows through a selected one of the sampler tubes in a first direction, then through the common end space in a radially inward direction, and then through the trap tube in an opposite direction.

Preferably, the magazine system has posts and post receiving spaces, with one of the posts fitting within only one of the spaces. This way, the sampler tubes can be readily and reliably positioned. A record is maintained of the selective supply of fluid through the sampler tubes, and the record is used during the analysis of the samples. The record can be correlated to the sampler tubes based on their position.

Sealing means are provided for preventing fluid communication between the atmosphere and the sampler tubes. Preferably, the sealing means maintains the sampler tubes within the magazine part when the magazine part is separated from the rest of the system.

Preferably, the separated part can be replaced with another magazine part to thereby replace the sampler tubes with a second set of sampler tubes. Fluid can then be selectively supplied through the second set of sampler tubes to thereby obtain a second set of samples while the first set of samples is at a laboratory or the like for analysis.

Other objects, features and advantages of the present invention will become apparent from the following detailed description of preferred embodiments of the invention, with reference to the accompanying drawings.

DETAILED DESCRIPTION OF THE PREFERRED EMBODIMENTS

Figure 1:
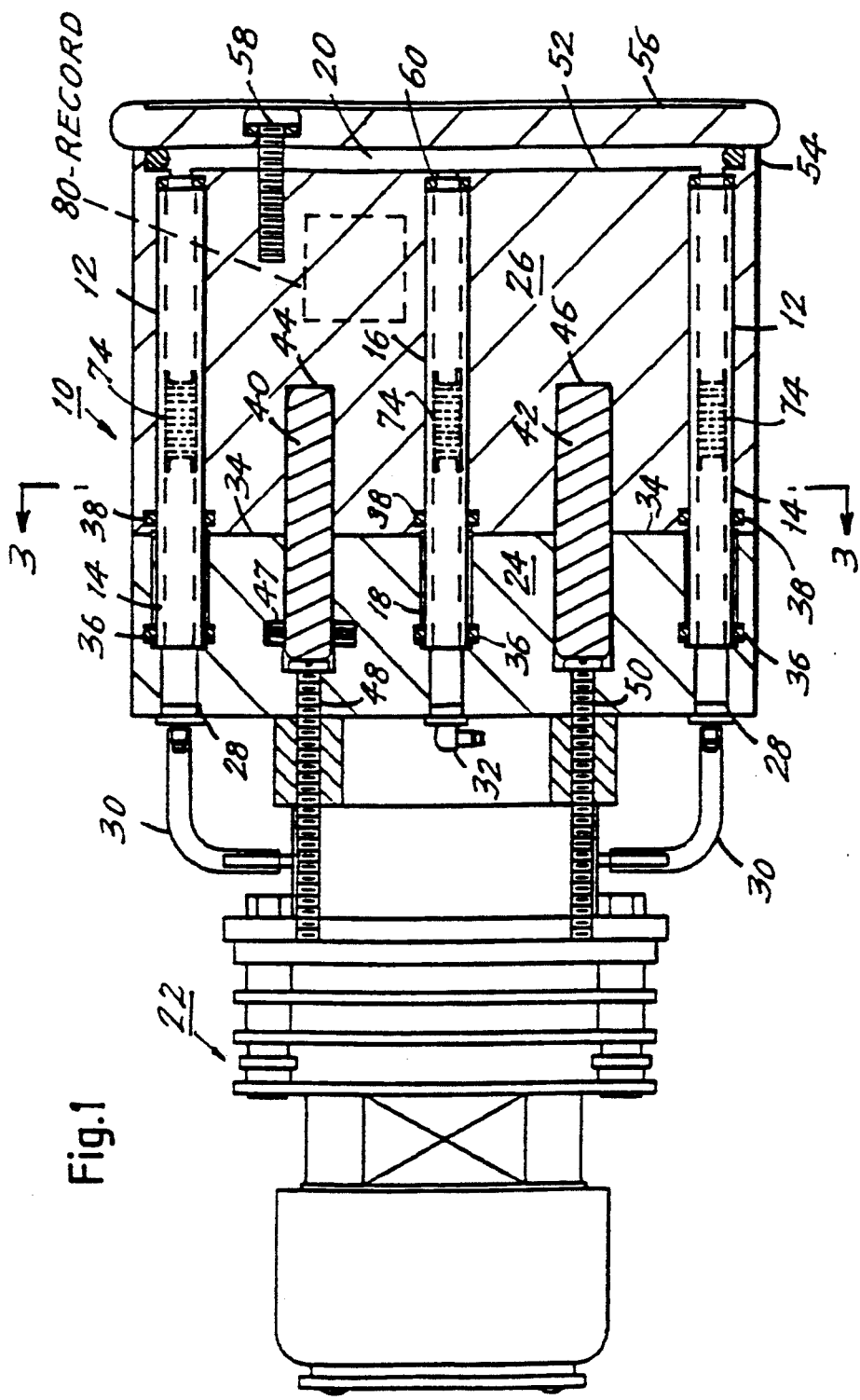
FIG. 1 is a cross-sectional view of a sampler in accordance with the present invention.

Referring now to the drawings, wherein like reference numerals indicate like elements, there is shown in FIG. 1 a system for taking samples which is constructed in accordance with the present invention. The system is formed of a magazine system 10 which has a plurality of spaces 12 for receiving sampler tubes 14, a space 16 for receiving a trap tube 18, and a common end space 20 for providing fluid communication between the trap tube 18 and each of the sampler tubes 14. The system also has a selector valve system 22 for selectively (e.g., sequentially or according to a program) directing fluid through the sampler tubes 14.

In operation, fluid flows through a selected one (or more) of the sampler tubes 14 (as determined by the selector valve system 22), then through the end space 20, and then through the trap tube 18. The valve system 22 then selects a second one (or more) of the tubes 14, and fluid is directed through the second tube 14, through the end space 20, and through the trap tube 18. Eventually, a separate sample of a constituent of the fluid is retained within each of the tubes 14 and a record of the operation of the selector valve system 22 is maintained for use in subsequent analysis of the samples. The purpose of the trap tube 18 is to prevent backflow into the common or end space 20.

The magazine system 10 is formed in two parts, i.e., with a fixed part 24 and a separable magazine part 26. The fixed part 24, which is bolted to the selector valve system 22, has a plurality of inlets 28 each of which is connected to the selector valve system 22 by a conduit 30. The inlets 28 and the conduits 30 connect the system 22 to the sampler tubes 14, respectively. The fixed part 24 also has an outlet 32 for connecting the trap tube 18 to a -pumping system (not illustrated). The pumping system draws air through the system 10 at a constant, low flow rate.

In the assembled position illustrated in FIG. 1, the parts 24, 26 are in contact with each other along a planar seam 34. Two sets of O-rings 36, 38 prevent fluid communication through the seam 34 between the atmosphere and the sampler tubes 14 Advantageously, the O-rings 38 fit more snugly against the sides of the sampler tubes 14 than do the O-rings 36. As a result, the sampler tubes 14 remain within the separable part 26 when the part 26 is separated from the fixed part 24. That is, the tubes 14 slide out of the O-rings 36 and are retained within the separable part 26 by the O-rings 38. The trap tube 18 is similarly retained within the separable magazine part 26. Further, the O-rings 36 are located very close (e.g., about 1/16 inch) to the left-most ends of the tubes 14, 18 (as viewed in FIG. 1). Therefore, even if the tubes 14, 18 are pulled somewhat out of the magazine part 26 by the O-rings 36 when the magazine part 26 is separated from the fixed part 24, the tubes 14, 18 will not likely be pulled out very far before the short or brief engagement of the O-rings 36 is broken free.

In the preferred embodiment, the diameter of the receiving spaces 12, 16 within the magazine part 26 is slightly less than the diameter of the spaces 12, 16 within the fixed part 24. This serves at least three functions: (1) It accommodates for any misalignment between the magazine part 26 and the fixed part 24. (2) It provides play so that the magazine part 26 and the tubes 14, 18 can be worked or wiggled away from the fixed part 24. (3) It helps ensure that the tubes 14, 18 remain within the magazine part 26 when the magazine part 26 is separated from the fixed part 24.

The correct registration or positioning of the parts 24, 26 with respect to each other is ensured by a set of posts 40, 42 which fit within post receiving spaces 44, 46. The post 42 is wider than the post 40 and will only fit within the space 46. The location of each of the sampler tubes 14 is correlated with the positioning of the post receiving space 46. This way, a record of when and how much fluid is selectively supplied through each of the conduits 30 by the selector valve system 22 can be correlated to the particular sampler tubes 14 located within the separable magazine part 26.

The posts 40, 42 preferably remain with the magazine part 26. When the magazine part 26 is assembled to the fixed part 24, the posts 40, 42 are frictionally retained within the fixed part 24 by O-rings 47. There may be an O-ring 47 for each of the posts or pins 40, 42, although only one such O-ring 47 is illustrated in the drawings.

Preferably, the posts 40, 42 fit slightly more tightly within the spaces 44, 46 than do the tubes 14, 18 within the spaces 12, 16. This helps prevent breakage of the tubes 12, 16.

The post receiving spaces 44, 46 also accommodate the bolts 48, 50 for connecting the fixed part 24 of the magazine system 10 to the selector valve system 22 and thereby advantageously reduce the length of the bolts 48, 50.

The common end space 20 is defined by an end surface 52, a peripheral sealing means 54 and an end plate 56. The cover 56 is bolted at 58 to the separable magazine part 26. This arrangement reduces the overall space needed for the system and also reduces the amount of flow volume between the sampler tubes 14 and the trap tube 18. This way, there is very little fluid which can flow from the inlet end 60 of the trap tube 18 back to the sampler tubes 14.

Figure 2:
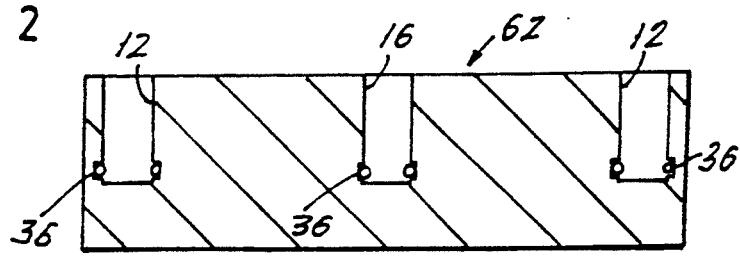
FIG. 2 is a cross-sectional view of a cover for the sampler of FIG. 1.

A cover 62 (FIG. 2) may be used to protect the exposed ends of the tubes 14 when the magazine part 26 is separated from the fixed part 24. The cover 62 is essentially identical in structure to the fixed part 24, except that it has no inlets 28 or outlet 32, and therefore completely covers the tubes 14, 18 to seal the ends of the tubes 14, 18 from the atmosphere. The separable part 26, the cover 62, and the tubes 14, 18 located therein form a transportable unit.

During the taking of the samples, a record is kept of parameters related to the sampling, e.g., when and for how long air is drawn through each of the sampler tubes 14. This record may be kept with and transported with the unit 26, 14, 18. For example, the record (shown schematically at 80 in FIG. 1) may be printed on a sheet of paper by a printer located in the vicinity of the valve system 22 and the paper may be wrapped around the unit 26, 14, 18 and held in place by a rubber band. A correlation between the record and the sampler tubes 14 located within the unit 26, 14, 18 can be easily made since the tubes 14 are retained within the tube receiving spaces 12, the spaces 12 are numbered or otherwise identified, and the positional relationship between the spaces 12 and the selector valve system 22 is ensured by the different sized posts 40, 42 and spaces 44, 46.

While the unit 26, 14, 18 is at the laboratory for analysis, the selector valve system 22 may remain on location and a second unit which is identical to the first unit, i.e., which also has sampler tubes and a trap tube received therein may be placed against the fixed part 24 to form a new magazine system. Operation of the selector valve system 22 then resumes and selective sampling continues with the system 22 selectively supplying fluid through the second set of sampler tubes. A correlation between the second set of sampler tube receiving spaces and the selector valve system 22 is automatically obtained by the posts 40, 42 and the spaces 44, 46.

Figure 3:
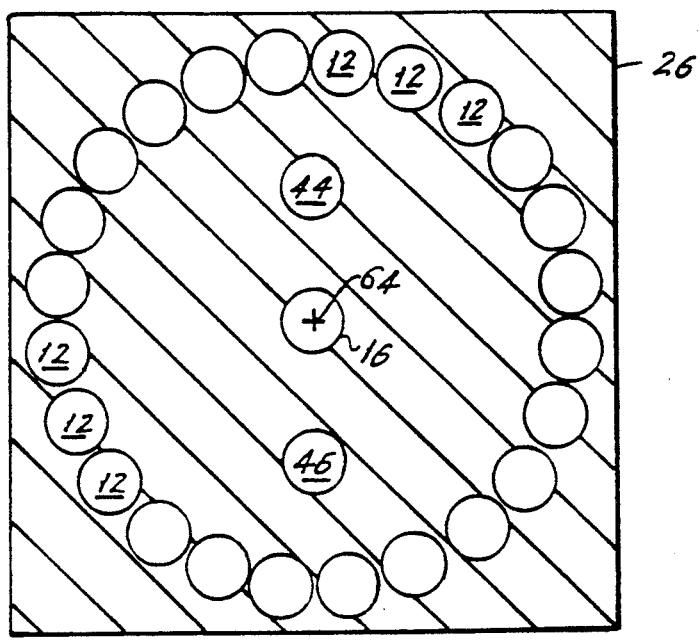
FIG. 3 is a cross-sectional view along line 3—3 of FIG. 1, with tubes removed.

Preferably, each sampler tube 14 is snugly retained concentrically within each of the spaces 12. Preferably, as illustrated in FIG. 3, there are twenty-four of the sampler tube receiving spaces 12, arranged in a circle around a central axis 64 of the magazine system 10, with their axes parallel to the axis 64. The axis of the trap tube receiving space 16 and the trap tube 18 (which is snugly received within the space 16) is coincident with the axis 64.

Figure 4:
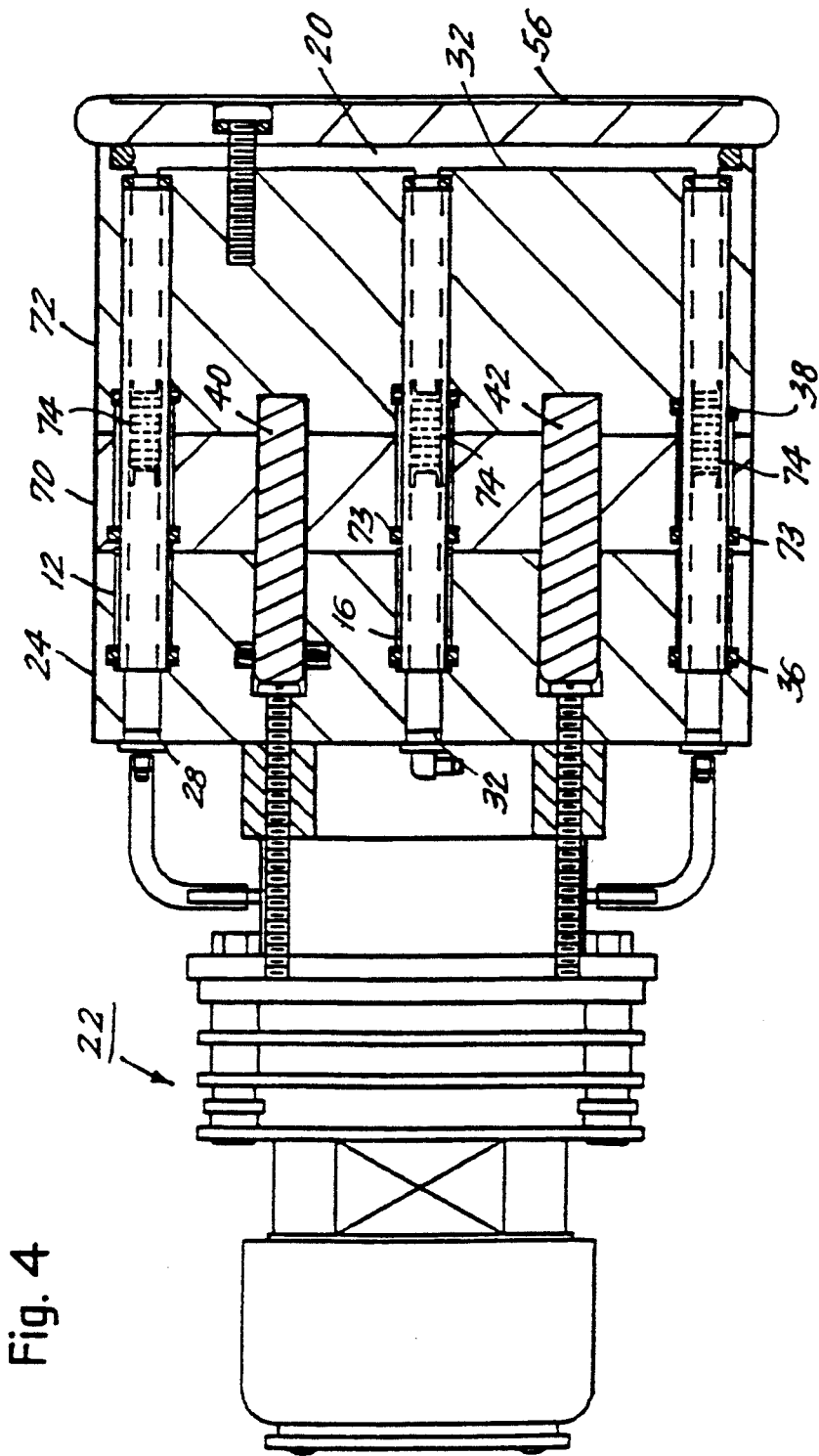
FIG. 4 is a cross-sectional view of a another sampler in accordance with the present invention.

In an alternative embodiment illustrated in FIG. 4, the separable magazine part has an inner part 70 and an outer part 72. The inner part 70 can be removed when shorter sampler tubes are used. That is, to take samples within short sampler tubes, the inner part 70 is not used and the outer part 72 is in contact with the fixed part 24. The inner part 70 is used when samples are taken within longer sampler tubes, as illustrated in FIG. 4. The inner part 70 may have O-rings 73 for providing the desired mechanical tolerance or fit.

The tubes 14, 18 themselves are conventionally formed of long cylinders of glass or plastic with adsorbent or absorbent material 74 therein. The constituents to be sampled are retained by the sorbent material 74. The tubes 14 can be identical to each other. There is no need for indicia to distinguish the tubes 14 from each other since the tubes 14 are identified by the spaces 12 within which they are received.

In a preferred embodiment, the samples may be desorbed from the material 74 at the laboratory without ever removing the sampler tubes 14 from the magazine part 26, 72.

Figure 5:
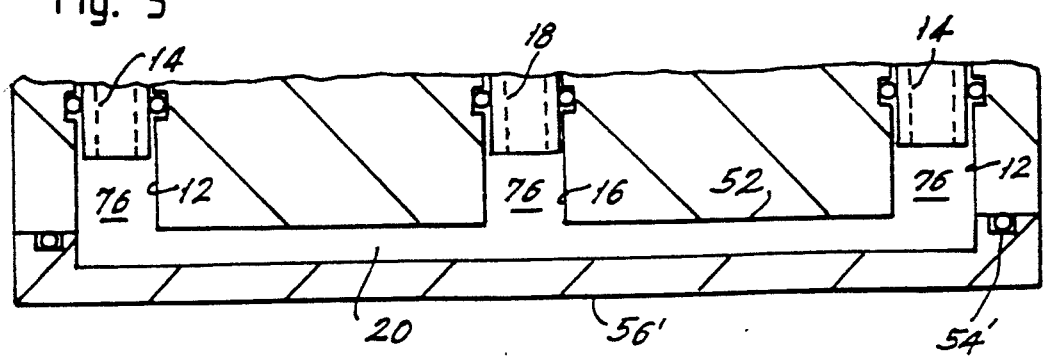
FIG. 5 is a partial, cross-sectional view of an alternative magazine part in accordance with the present invention.

As illustrated in FIG. 5, the peripheral sealing means 54' which defines the common end space 20 may be an element of the end plate 56'. Further, the ends 76 of the sampler and trap tube receiving spaces 12, 16 may open out through the end surface 52 in such a way as to simplify manufacture and allow the tubes 14, 18 to be inserted and withdrawn through the end surface 52. In this embodiment, posts attached to the end plate 56' or another suitable means may be provided to prevent the tubes 14, 18 from sliding downwardly (as viewed in FIG. 5) past the end surface 52 as the magazine part 26 is assembled against the fixed part 24.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A sampler magazine system, comprising:
    a plurality of sampler tube receiving spaces for receiving sampler tubes;
    a first part which includes a plurality of introducing means disposed in said first part for introducing gaseous fluid into corresponding ones of the sampler tubes; and a second part which forms with the sampler tubes a replaceable magazine which is readily removable with the sampler tubes from the first part and which includes at least a portion of each of the sampler tube receiving spaces, whereby the second part and the sampler tubes are separable as a unit from the means for introducing the fluid into the sampler tubes, and whereby the introducing means and the corresponding receiving spaces are simultaneously brought into fluid communication with each other when the first and second parts are connected together.

2. The sampler magazine system of claim 1, further comprising:

a trap tube receiving space which is adjacent to the sampler tube receiving spaces; and a common end space for providing fluid communication between the trap tube receiving space and each of the sampler tube receiving spaces, the common end space being within the second part.

3. The sampler magazine system of claim 2, further comprising a selector valve system for selectively introducing said gaseous fluid into the sampler tube receiving spaces such that said fluid flows through a selected one of the sampler tubes.

4. The sampler magazine system of claim 3, wherein the fluid flows into a common space from the selected tube, and then flows into a trap tube associated with the sampler tubes.

5. The sampler magazine system of claim 4, wherein the fluid flows through the selected tube in a first direction, then through the common space in a second direction, and then through the trap tube in a direction which is opposite to the first direction.

6. The sampler of claim 1, further comprising recording means associated with the second part and adapted for recording information relative to the fluid introduced into the sampler tubes.

7. The sampler of claim 6, wherein said recording means is adapted for recording information relative to fluid introduced into each respective sampler tube as a function of the position of the respective tube within the second part.

8. A sampler, comprising:
(A) a magazine system which includes:
 (1) a plurality of sampler tube receiving spaces for receiving sampler tubes, each of the sampler tubes receiving spaces having a central, elongated axis, the axes of the sampler tube receiving spaces being parallel to each other;
 (2) a trap tube receiving space for receiving a trap tube, the trap tube receiving space being surrounded by the sampler tube receiving spaces, the trap tube receiving space having an elongated, central axis which parallel to the axes of the sampler tube receiving spaces; and
 (3) a common end space for providing fluid communication between the trap tube receiving space and each of the sampler tube receiving spaces; and
(B) a selector valve system for selectively introducing fluid into the sampler tube receiving spaces such that fluid flows through a selected one of the sampler tubes in a first direction, then through the common end space in a radially inward direction, and then through the trap tube in a second direction, the second direction being opposite to the first direction; and wherein the magazine system includes first and second parts which are separable from each other, the first part including means for providing fluid communication between the selector valve system and the sampler tubes, the second part including the common end space and at least a portion of each of the sampler tube receiving spaces, whereby the second part and the sampler tubes are separable from the selector valve system and the first part of the magazine system.

9. The sampler of claim 8, further comprising the sampler tubes and the trap tube, the sampler tubes and the trap tube including extracting means for extracting material to be sampled from fluid flowing through the sampler and trap tubes.

10. The sampler of claim 9, wherein the extracting means includes means for adsorbing or absorbing material from air flowing through the sampler and trap tubes.

11. The sampler of claim 8, further comprising positioning means for correctly positioning the sampler tubes with respect to the selector valve system.

12. The sampler of claim 11, wherein the positioning means includes posts which extend between the first and second parts of the magazine system, and spaces for receiving the posts, wherein one of the posts will fit within only one of the spaces for receiving the posts.

13. The sampler of claim 8, further comprising a cover for covering the sampler tubes when the second part of the magazine system is separated from the first part of the magazine system.

14. The sampler of claim 13, wherein the cover, the second part, and the sampler tubes located therein form a transportable unit.

15. The sampler of claim 8, wherein the second part of the magazine system has an end surface, the sampler further comprising an end plate which is secured to the second part of the magazine system, the common end space being defined by the end surface and the end plate.

16. The sampler of claim 8, wherein the first and second parts define a seam therebetween, the magazine system including sealing means for preventing fluid communication between the atmosphere and the sampler tubes through the seam.

17. The sampler of claim 16, wherein the sealing means maintains the sampler tubes within the second part of the magazine system when the second part is separated from the first part of the magazine system.

18. The sampler of claim 17, wherein the sealing means includes first and second sets of O-rings, the first set of O-rings being located within the first part of the magazine system, the second set of O-rings being located within the second part of the magazine system, wherein the second set of O-rings fit more snugly against the sampler tubes than do the first set of O-rings.

19. The sampler of claim 17, wherein the sealing means includes first and second sets of O-rings, the first set of O-rings being located within the first part of the magazine system, the second set of O-rings being located within the second part of the magazine system, wherein the first set of O-rings are arranged so as to be close to the ends of the sampler and trap tubes, whereby the sampler and trap tubes remain within the second part of the magazine when the second part is separated from the first part.

20. The sampler of claim 8, wherein the magazine system includes a third part which is located between the first and second parts, the third part being separable from the first and second parts, each of the sampler tube receiving spaces being located within the first, second and third parts of the magazine system, whereby the sampler is operable with sampler tubes having different lengths.

21. The sampler of claim 8, wherein the sampler tube receiving spaces have a smaller diameter within the second part than within the first part.

22. The sampler of claim 8, further comprising registration posts which interconnect the first part and the second part and which locate the first and second parts in a predetermined positional relationship.

23. The sampler of claim 22, wherein the registration posts have a predetermined positional relationship with the sampler tube receiving spaces.

24. The sampler of claim 22, wherein the registration posts fit within spaces in the second part slightly more tightly than the sampler tubes fit within the second part.

* * * * *